(12) United States Patent
Odidi et al.

(10) Patent No.: US 6,893,661 B1
(45) Date of Patent: May 17, 2005

(54) CONTROLLED RELEASE FORMULATIONS USING INTELLIGENT POLYMERS

(75) Inventors: Isa Odidi, Toronto (CA); Amina Odidi, Toronto (CA)

(73) Assignee: Biovail Corporation, Mississauga (CA)

( * ) Notice: Subject to any disclaimer, the term of this patent is extended or adjusted under 35 U.S.C. 154(b) by 0 days.

(21) Appl. No.: 09/403,437

(22) PCT Filed: Apr. 3, 1998

(86) PCT No.: PCT/CA98/00274

§ 371 (c)(1),
(2), (4) Date: Dec. 20, 1999

(87) PCT Pub. No.: WO98/47491

PCT Pub. Date: Oct. 29, 1998

Related U.S. Application Data

(60) Provisional application No. 60/036,551, filed on Apr. 21, 1997.

(51) Int. Cl.[7] ............................ A61K 9/22; A61K 9/26; A61K 9/32
(52) U.S. Cl. ................. 424/468; 424/469; 424/470; 424/482
(58) Field of Search ................. 424/468, 469, 424/470, 482, 464, 465, 474, 484, 486

(56) References Cited

U.S. PATENT DOCUMENTS

| | | | |
|---|---|---|---|
| 4,167,558 A | 9/1979 | Sheth et al. | |
| 4,259,314 A | 3/1981 | Lowey | |
| 4,308,251 A | 12/1981 | Dunn et al. | |
| 4,361,545 A | 11/1982 | Powell et al. | |
| 4,389,393 A | 6/1983 | Schor et al. | |
| 4,525,345 A | 6/1985 | Dunn et al. | |
| 4,556,678 A | 12/1985 | Hsiao | |
| 4,601,894 A | 7/1986 | Hanna et al. | |
| 4,680,323 A | 7/1987 | Lowey | |
| 4,687,757 A | 8/1987 | Parrott et al. | |
| 4,692,337 A | 9/1987 | Ukigaya et al. | |
| 4,695,591 A | 9/1987 | Hanna et al. | |
| 4,756,911 A | 7/1988 | Drost et al. | |
| 4,853,249 A | * 8/1989 | Takashima et al. | ......... 424/468 |
| 4,968,509 A | 11/1990 | Radebaugh et al. | |
| 4,994,276 A | 2/1991 | Baichwal et al. | |
| 5,000,962 A | * 3/1991 | Sangekar et al. | ........... 424/482 |
| 5,073,380 A | 12/1991 | Babu et al. | |
| 5,162,117 A | * 11/1992 | Stupak et al. | ............... 424/475 |
| 5,264,446 A | 11/1993 | Hegasy et al. | |
| 5,417,982 A | 5/1995 | Modi | |
| 5,439,687 A | 8/1995 | Compassi | |
| 5,451,409 A | 9/1995 | Rencher et al. | |
| 5,462,747 A | 10/1995 | Radebaugh et al. | |
| 5,484,608 A | 1/1996 | Rudnic et al. | |
| 5,543,154 A | 8/1996 | Rork et al. | |
| 6,083,532 A | * 7/2000 | Zhang et al. | ............... 424/468 |

FOREIGN PATENT DOCUMENTS

| | | |
|---|---|---|
| EP | 0157695 | 9/1985 |
| EP | 0226884 | 7/1987 |
| EP | 0253490 | 1/1988 |
| EP | 0468436 | 1/1992 |
| JP | 03-206039 | 9/1991 |

OTHER PUBLICATIONS

Lin et al, *European Journal of Pharmaceutics and Biopharmaceutics*, 42(3):193–198 (1996).

* cited by examiner

*Primary Examiner*—James Spear
*Assistant Examiner*—Retford Berko
(74) *Attorney, Agent, or Firm*—Dinsmore & Shohl LLP

(57) ABSTRACT

An extended release dosage composition of pharmaceutically active substances that have a water contact angle (θ) such that cos θ is between +0.9848 and −0.9848 presented as a matrix tablet containing the said pharmaceutically active substances, with/without suitable pharmaceutical excipients in intimate mixture with two groups of intelligent polymers having opposing wettability characteristics, one demonstrating a stronger tendency towards hydrophobicity and the other a stronger tendency towards hydrophilicity, the polymer combination being between the ratios of 1:50 and 50:1 amounts effective to control the release of said pharmaceutically active substances in a mathematically predictable manner, wherein the polymer demonstrating a stronger tendency towards hydrophobicity is not less than 5% wt/wt and preferably between 5–70% wt/wt of the final formulation composition. The intelligent polymers being ethylcellulose (EC) as a more strongly hydrophobic and hydroxyethylcellulose (HEC) and/or hydroxypropyl methylcellulose (HPMC) as more strongly hydrophilic (the ratio of HEC to HPMC being between 1:100 and 100:1). The matrix tablet is optionally coated with an enteric coat, 0–5%–15% wt/wt to prevent the initial burst effect seen in such systems and to impart gastrointestinal tract (GIT) "stealth" characteristics especially in the presence of food.

34 Claims, No Drawings

CONTROLLED RELEASE FORMULATIONS USING INTELLIGENT POLYMERS

This application claim the benefit of Provisional Application No. 60/036,551, filed Apr. 27, 1997.

FIELD OF THE INVENTION

The present invention is directed to novel controlled release formulations of pharmaceutically active substances and methods for their preparation. More particularly, the present invention relates to an easily absorbable, controlled release pharmaceutical formulation utilizing groups of intelligent polymers having opposing wettability characteristics.

BACKGROUND OF THE INVENTION

Controlled release formulations of pharmaceutical agents is an extremely large market in the pharmaceutical and medical fields. A number of types of controlled release dosage forms are known, including matrix tablet systems incorporating active ingredients, fillers and various types of excipients. The very different properties of numerous different types of pharmaceutically active ingredients has necessitated the development of a number of different drug delivery systems utilizing polymer technology in order to provide an appropriate release of a particular medicament after oral ingestion by a patient.

U.S. Pat. Nos. 4,601,894 and 4,687,757 describe a controlled release drug delivery system which contains hydroxypropyl cellulose (HPMC) and a second polymer such as ethylcellulose, methylcellulose, sodium carboxymethyl cellulose or other cellulose ethers. U.S. Pat. No. 4,680,323 describes a carrier system comprising hydroxypropyl cellulose and a carboxy vinyl polymer. U.S. Pat. No. 4,695,591 describes the use of HPMC for mediating controlled release of pharmaceutically active substances. U.S. Pat. No. 4,994,276 teaches a free-flowing directly compressible granulation useful as a slow release pharmaceutical excipient. The excipient includes a hydrophilic matrix which includes a heteropolysaccharide and a polysaccharide material capable of cross-linking the heteropolysaccharide.

U.S. Pat. No. 4,167,558 teaches a novel sustained release tableted formulation for oral administration. The formulation is hydrodynamically balanced to be buoyant in gastric juice thereby remaining in the stomach for an extended period of time. U.S. Pat. No. 4,259,314 teaches a method and composition for the preparation of controlled long-acting pharmaceuticals using a dry carrier or base material comprising an effective amount of hydroxypropyl methylcellulose and hydroxypropyl cellulose suitable for use with both hygroscopic and non-hygroscopic materials. The controlled long-acting products of the invention are suitable for use in the form of lozenges, bucal tablets, oral tablets or suppositories.

U.S. Pat. No. 4,308,251 teaches a tablet formulation comprising an effective amount of an active acidic therapeutic agent, a release-controlling agent and an erosion-promoting agent in relative amounts to provide a criticality factor of less than 450, and in proportions of release-controlling and erosion-promoting agent, respectively, between 0.8–1.6 and 1.0–7.5 weight percent per tablet. The tablets of this invention exhibit zero order release in vitro and closely approximate zero order absorption in vivo.

U.S. Pat. No. 4,361,545 teaches a class of solid pharmaceutical formulations which provides slow, zero order in vivo release of a wide range of pharmaceutically active ingredients upon oral administration. A broad range of release rates can be preselected by suitable adjustments of tablet properties. The formulations are based upon control of active ingredient release from the surface of the tablet via a controlled surface erosion mechanism.

U.S. Pat. No. 4,389,393 teaches a carrier base material combined with a therapeutically active medicament and shaped and compressed to a solid unit dosage form having a regular and prolonged release pattern upon administration, the carrier base material being one or more hydroxypropylmethylcelluloses or a mixture of one or more hydroxypropylmethylcelluloses having a methoxy content of 16–24 weight %, a hydroxypropoxyl content of 4–32 weight % and an average molecular weight of at least 50,000.

U.S. Pat. No. 4,525,345 teaches a constant release rate indomethacin formulation in tablet unit dosage form containing an admixture of from 50 to 200 mg of indomethacin, from about 1.7 to 3.7 weight percent of a slow-dissolving, water-insoluble cellulose derivative, from about 1.5 to 5.0 weight percent of a tableting disintegrant, and from about 40 to 80 weight percent of a pharmaceutically acceptable bulking agent or diluent.

U.S. Pat. No. 4,556,678 teaches a tablet consisting essentially of a therapeutically effective amount of propranolol to provide a sustained release thereof over a prolonged period of time. The tablet comprises compressed granules having from about 0.1 to about 10 parts by weight hydroxypropyl methylcellulose and about one part by weight hydroxpropyl cellulose.

U.S. Pat. No. 4,692,337 teaches a sustained release pharmaceutical tablet comprising theophylline and ethyl cellulose uniformly dispersed therein in an amount of 5 to 200 parts by weight of ethyl cellulose based on 100 parts by weight of the theophylline.

U.S. Pat. No. 4,756,911 teaches a controlled release pharmaceutical formulation in the form of a coated tablet, containing a core portion from which medicament, such as procainamide hydrochloride, is slowly released over a controlled length of time. The core also includes one or more primary hydrocolloid gelling agents which is a hydropropymethyl cellulose having a viscosity of within the range of from about 1,000 to about 6,000 centipoises in 2% solution at 20° C., a methoxyl content of 28–30% and optionally a secondary hydrocarbon gelling agent, such as hydroxpropyl cellulose and/or methyl cellulose.

U.S. Pat. No. 5,073,380 teaches a pharmaceutical sustained release tablet containing a pharmaceutical active, hydroxyethyl cellulose, a wicking agent, povidone, pregelatinized starch, lubricant and a glidant.

U.S. Pat. No. 5,417,982 teaches a controlled release formulation for use with a variety of drugs or hormones in microspherical form. The drug or hormone, e.g. bovine somatropine, is suspended in a polymer matrix formed from at least two highly water soluble biodegradable polymers. The microspheres are coated with a (δ, 1 lactide-glycolide) copolymer.

U.S. Pat. No. 4,968,509 teaches an acetaminophen-sustained release tablet formed by making a wet granulation, using Povidone (PVP) in water or alcohol-water as the granulating fluid which is mixed with acetaminophen, hydroxyethyl cellulose, a wicking agent e.g. microcrystalline cellulose, then drying and milling the granulation and blending with dry powdered erosion promoter, e.g. pregelatinized starch, wicking agent, lubricant e.g. magnesium stearate and glidant e.g. silicon dioxide, and compressing the resultant granulation.

U.S. Pat. No. 5,462,747 teaches a pharmaceutical sustained release homogeneous tablet formed by making a wet granulation using povidone (PVP) in alcohol as the granulating fluid mixed with a pharmaceutical active, ethylcellulose, a wicking agent, e.g. microcrystalline cellulose, an erosion promoter, e.g. pregelatinized starch, then drying and milling the granulation and blending with a dry powdered erosion promotor, wicking agent, lubricant and glidant.

U.S. Pat. No. 5,543,154 teaches a device for the controlled delivery of a beneficial agent as a gelatinous dispersion consisting of a core which contains a beneficial agent, a polymer which forms gelatinius micoroscopic particles upon hydration and if desired an agent to modulate the hydration of the polymer; and an impermeable, insoluble coating which adheres to and surrounds the core and contains apertures which provides an area for the hydration and release of a disperson comprising gelatinous microscropic particles.

U.S. Pat. No. 5,439,687 teaches pharmaceutical dosage forms for the daily oral administration of nifedipine or of another calcium antagonist of the dihydrophyridine type, characterised by the homogeneous matrix containing 2–50% by weight of hydroxypropylmethylcellulose having an average molecular weight of 20,000–250,000, 5–60% by weight of a calcium antagonist of the dihydropyridine type, as well as excipients compatible with the formulation.

U.S. Pat. No. 5,264,446 teaches a solid pharmaceutical composition of nifedipine crystals having specific surface area of 1–4 $m^2/g$ in the form of tablets, pills, drages, capsules, suppositories, sachets or two layer tablets resulting in sustained release.

While these systems can provide for sustained release of a selected active ingredient, most of these systems have the disadvantage of being affected by the presence of food and gastrointestinal engines in the gastrointestinal (GI) tract. Therefore, the active ingredient is often not delivered consistent and reproducible manner. In addition, osmotic and press coated tablets are particularly difficult and expensive to manufacture.

It is therefore particularly desirable to design an efficient drug delivery system that is capable of controlled drug delivery of both high dose, highly soluble, hydrophillic and low dose, poorly soluble, hydrophobic pharmaceutically active substance(s) into the gastrointestinal tract (GIT) in order to provide sustained therapeutic effects for over 24 hours with only a single dose and without any food effect. It is also highly desirable to develop a drug delivery system that is relatively easy and inexpensive to manufacture and more efficient in providing a sustained release of pharmaceutical agents than the known controlled delivery systems.

SUMMARY OF THE INVENTION

An object of the present invention is to provide a novel controlled sustained release delivery composition which may contain a wide variety of pharmaceutically active ingredients and which demonstrates good absorbability of the selected active ingredient and a maintenance of the therapeutically effective blood level of the pharmaceutically active ingredient for a long duration of time by one time administration. This novel controlled release composition and system has been named intelliGITransporter™.

According to an object of the present invention there is provided a novel controlled release delivery composition comprising at least one selected pharmaceutically active ingredient incorporated within a homogeneous matrix comprising effective amounts of two intelligent polymers having opposing wettability characteristics, wherein one polymer is selected which demonstrates a stronger tendency towards hydrophobicity and the other polymer is selected which demonstrates a stronger tendency towards hydrophilicity.

Preferably, the active pharmaceutical ingredient selected has a water contact angle ($\theta$) such that cos $\theta$ is between +0.9848 and −0.9848. Also, preferably the intelligent polymer demonstrating a stronger tendency towards hydrophobicity is ethylcellulose (EC) whereas the intelligent polymer demonstrating a stronger tendency towards hydrophilicity is hydroxyethylcellulose (HEC) and/or hydroxypropyl methylcellulose (HPMC).

It is still further objective of the present invention to provide a controlled release delivery composition wherein the selection of the pharmaceutically active ingredient, the physiochemical properties, the proportion of polymer blend and the wettability of the pharmaceutically active substance (s) provides effective controlled release of the pharmaceutically active substance(s).

It is yet a further object of the present invention to provide an effective drug is delivery composition that is capable of controlled drug delivery of both high dose, highly soluble hydrophilic or low dose poorly soluble hydrophobic pharmaceutically active substance(s) to the gastrointestinal tract with a zero or first order kinetics.

In accordance with a further object of the present invention is a device for providing a controlled release of a pharmaceutically active ingredient contained therein, the device comprising at least one selected pharmaceutically active-ingredient incorporated within a homogeneous matrix comprising effective amounts of two intelligent polymers having opposing wettability characteristics, wherein one polymer is selected which demonstrates a stronger tendency towards hydrophobicity and the other polymer is selected which demonstrates a stronger tendency towards hydrophilicity.

The composition and device of the present invention can be provided as a tablet and may be optionally encased in a coating material which prevents the burst and/or food effect associated with orally ingested medicaments and imparts gastrointestinal stealth characteristics. The encoated matrix providing controlled release kinetics comparable to those of osmotic or press coated controlled release devices. The composition may be provided for oral administration or as a suppository depending on the chosen pharmaceutical active agent selected therein.

It is yet a further objective of the present invention to provide a controlled release drug delivery system for the effective delivery of one or more of the following pharmaceutically active ingredients: nifedipine, nicardipine, felodipine, captopril, naproxen, diclofenac, terfenadine, pentoxifylline, fenofibrate, glipizide, buspirone, cisapride, verapamil, diltiazem, aciclovir, zidovudine, pilocarpine, moclobemide, lamotrigine, risperidon, clonazepam, nefazodone, lovastatin, simvastatin, pravachol, ketorolac, hydromorphone, morphine, ticlopidine, seligiline, venlafaxine, alprazolam, carbamazepine, divalproex and phenytoin.

It is also a further objective of the present invention to provide controlled delivery of therapeutic agents selected from the group consisting of anti-histamines, anti-depressants, anti-viral agents, anesthetics, antacids, anti-arthritics, antibiotics, anti-psychotics, anti-spasmodics, anxiolytic agents, appetite suppressants, cardiovascular agents, cough suppressants, emollients, gastro-intestinal agents, growth regulators, hypoglycemic agents, respiratory stimulants, vitamins, angiotensin converting enzyme inhibitors, anti-asthmatics, anti-cholesterolemics, anti-convulsants, anti-depressants, anti-diarrhea preparations, anti-infectives, anti-inflammatory agents, anti-nauseants, anti-stroke agents, anti-tumor drugs, anti-tussives, anti-uricemic drugs, amino-acid preparations, antiemetics, anti-obesity drugs, antiparasitics, antipyretics, appetite stimulants, cerebral dilators, chelating agents, cholecystokinin antagonists, cognition activators, deodorants, dermatological agents, diabetes agents, diuretics, erythropoietic drugs, fertility agents, synthetic hormones, laxatives, mineral supplements, neuroleptics, neuromuscular agents, peripheral vaso-dilators, prostaglandins, vaginal preparations, vaso-constrictors and vertigo agents; acetaminophen, acetic acid, acetylsalicylic acid, buffered acetylsalicylic acid, albuterol, albuterol sulfate, ethanol isopropanol, allantoin, aloe, aluminum acetate, aluminum carbonate, aluminum chlorohydrate, aluminum hydroxide, alprozolam, amino acids, aminobenzoic acid, amoxicillin, ampicillin, amsacrine, amsalog, anethole, aspartame, atenolol, bacitracin, balsam peru, beclomethasone dipropionate, benzocaine, benzoic acid, benzophenones, benzoylperoxide, biotin, bisacodyl, bornyl acetate, bromophenieramine maleate, bupropion, caffeine, calamine, calcium, calcium carbonate, calcium casinate, calcium hydroxide, camphor, captopril, cascara sagrada, castor oil, cefaclor, cefadroxil, cephalexin, cetylalcohol, cetylpyridinium chloride, chelated minerals, chloramphenicol, chlorcyclizine hydrochloride, chlorhexidine gluconate, chloroxylenol, chloropentostatin, chlorpheniramine maleate cholestyramine resin, choline bitartrate, cimetidine hydrochloride, cinnamedrine hydrochloride, citalopram, citric acid, cocoa butter, cod liver oil, codeine and codeine phosphate, clonidine, clonidine hydrochloride, clorfibrate, ciprofloxacin HCl, cyanocobalamin, cyclizine hydrochloride, danthron, dexbrompheniranime maleate, dextromethorphan hydrobromide, diazepam, dibucaine diclofenac sodium, digoxin, dimethicone, dioxybenzone, diphenhydramine citrate, diphenhydramine hydrochloride, docusate calicum, docusate potassium, docusate sodium, doxycycline hyclate, doxylamine succinate, efaroxan, enalapril, enoxacin, erythromycin, estropipate, ethinyl estradiol ephedrine, epinephrine bitartrate, erythropoietin, eucalyptol, ferrous fumarate, ferrous gluconate, ferrous sulfate, folic acid, fosphenytoin, fluoxetine HCl, furosemide, gaba entan gentamicin, gemfibrozil, glipizide, glycerin, glyceryl stearate, griseofulvin, guaifenesin, hexylresorcinol, hydrochlorothiaxide, hydrocodone bitartrate, hydrocortisone, hydrocortisone acetate, 8-hydroxyquinotine sulfate, ibuprofen, indomethacin, inositol, insulin, iodine, ipecac, iron, isoxicam, ketamine, koalin, lactic acid, lanolin, lecithin, lidocaine, lidocaine hydrochloride, lifinopril, liotrix, lovastatin, magnesium carbonate, magnesium salicylate, magnesium trisilocate, mefenamic acid, meclofenanic acid, meclofenamate sodium, medroxyprogesterone acetate, methenamine mandelate, menthol, meperidine hydrochloride, metaproterenol sulfate, methyl nicotinate, methyl salicylate, methylcellulose, methsuximide, metromidazole, metromidazole hydrochloride, metoprolol tartrate, miconazole nitrate, mineral oil, minoxidil, morphine, naproxen sodium, neomycin sulfate, niacin, niacinamide, nicotine, nicotinamide, nitroglycerin, nonoxynol-9, norethindone, norethindone acetate, nystatin, octoxynol, octyl dimethyl PABA, octyl methoxycinnamate, omega-3 polyunsaturated fatty acids, omeprazole, oxolinic acid, oxybenzone, oxtriphylline, para-aminobenzoic acid (PABA), padimate, paramethadione, pentastatin, peppermint oil, pentaerythriol tetranitrate, pentobarbital sodium, pheniramine maleate, phenobarbital, phenol, phenolphthalein, phenylephrine hydrochloride, phenylpropanolamine, phenylpropanolamine, hydrochloride, phenytoin, phenelzine, sulfate, pirmenol, piroxicam, polymycin B sulfate, potassium chloride, potassium nitrate, prazepam, procianamide hydrochloride, procaterol, propoxyphene, propoxyphene HCl, propoxyphene napsylate, pramiracitin, pramoxine, pramoxine hydrochloride, propronolol HCl, psedoephedrine hydrochloride, pseudoephedrine sulfate, pyridoxine, quinapril, quinidine gluconate, quinestrol ralitoline, ranitadine, resorcinol, riboflavin, salicylic acid, sesame oil, shark liver oil, simethicone, sodium bicarbonate, sodium citrate, sodium fluoride, sodium monofluorophosphate, sulfanethoxazole, sulfur, tacrine, tacrine HCl, theophylline, tramadol, terfenidine, thioperidone, trimetrexate, triazolam, timolol maleate, tretinoin, tetracycline hydrochloride, tolmetin, tolnaftate, triclosan, triprolidine hydrochloride, undecylenic acid, vancomycin, vidaribine phosphate, vitamin A, vitamin B, vitamin C, vitamin D, vitamin E, vitamin K, witch hazel, xylometazoline hydrochloride, zinc, zinc sulfate, and zincundecylenate.

In accordance with another aspect of the present invention is a method for preparing a device for the controlled release of selected pharmaceutically active ingredients, the method comprising blending at least one selected pharmaceutically active substance having a water contact angle (θ) such that cos θ is between +0.9848 and −0.9848 with about 5 to 25% by weight hydrophillic polymer and about 1 to 25% hydrophobic polymer, adding suitable pharmaceutical excipients, surface active agents and lubricants, granulating the mixture with isopropyl alcohol, drying the granular mixture, milling the dried mixture, adding about 5 to 70% ethylcellulose, adding a lubricant and optionally a glidant and compressing the granules into tablets. The tablets are optionally encased in a gastrointestinal stealth encasement or a pharmaceutically acceptable film coat.

DETAILED DESCRIPTION OF THE PREFERRED EMBODIMENTS

The present invention provides a composition which provides controlled sustained release of pharmaceutically active ingredients and demonstrates stealth characteristics. The composition of the present invention provides a pseudo first order, first order or zero order release of pharmaceutically active substances that have a water contact angle (θ) such that cos θ is between +0.9948 and −0.9848. The composition may be presented as a matrix tablet in which the pharmaceutically active ingredients are intimately mixed with two groups of intelligent of polymers having opposing wettability characteristics, one demonstrating a stronger tendency towards hydrophobicity for example ethylcellulose (EC) and the other possessing a stronger a tendency towards hydrophilicity, for example ethydroxyethylcellulose (HEC) or hydroxypropyl methylcellulose (HPMC). The composition can be made with suitable pharmaceutically acceptable excipients, suitable surface active agents, lubricants, channeling agents and compression enhancers.

The amount of ethylcellulose in the composition should not be less than about 5% wt/wt, and preferably, is about 5% to about 70% wt/wt of the final formulation. The HEC and HPMC are present in a ratio of about 1:100 to about 100:1, the preferred ratio being from about 1:50 to about 50:1. Together, the intelligent polymers provide a homogeneous matrix for the pharmaceutically active ingredient and have the following single and three-component calculated solubility parameters (MPa$^{0.5}$) using the group contribution method.

| Wettability of polymer | δ | δ$_t$ | δ$_d$ | δ$_p$ | δ$_h$ | δ$_{-a}$ |
|---|---|---|---|---|---|---|
| More hydrophilic | 18–50 | 18–45 | 12–17 | 2–8 | 12–20 | 13–20 |
| More hydrophobic | 15–25 | 14–24 | 12–17 | 2–7 | 5–15 | 6–13 |

Where δ is the conventional Hildebrand parameter, t = total, d = dispersion, p = polar, h = hydrogen bond and a = association interactions.

Preferred excipients for use in the compositions of the present invention include glidants such as silicon dioxide which may be present in an amount of about 0.25% to 5% wt/wt. Suitable surface active agents may be present in the amount of about 0.5% to 15% wt/wt and include sodium lauryl sulfate. Channeling agents may be present in an amount of about 10% to 70% wt/wt and include anhydrous lactose. Suitable lubricants for use in the composition are present in an amount of about 0.1% to 5% and include magnesium stearate. An optional compression enhancer may be present in an amount of about 5% to 30% wt/wt and includes microcrystalline cellulose. Although the preferred excipients, surface active agents, lubricants, channeling agents, and compression enhancers are listed herein, it is understood by those skilled in the art that other suitable excipients, surface active agents, lubricants, channeling agents, and compression enhancers may also be used in the present invention. One skilled in the art would clearly understand the different types of excipients, surface active agents, channeling agents, and compression enhancers suitable for use in the present invention.

The pharmaceutically active ingredients are selected from those substances that have a water contact angle (θ) such that cos θ is between +0.9948 and −0.9848. The composition may contain one or more such active ingredients in an amount to provide therapeutically effective dosages. The pharmaceutically active ingredients may be selected from but are not limited to nifedipine, nicardipine, felodipine, captopril, naproxen, diclofenac, terfenadine, pentoxifylline, fenofibrate, glipizide, buspirone, cisapride, verapamil, diltiazem, aciclovir, zidovudine, pilocarpine, moclobemide, lamotrigine, risperidon, clonazepam, nefazodone, lovastatin, simvastatin, pravachol, ketorolac, hydromorphone, morphine, ticlopidine, seligiline, venlafaxine, alprazolam, carbamazepine, divalproex and phenytoin.

A most preferred pharmaceutically active ingredient is nifedipine which provides coronary vasodilating and hypotensive effects. As this medicament is hardly water soluble, has little absorbability in body fluids and is rapidly metabolized and excreted, it is highly advantageous to provide nifedipine in the controlled release composition of the present invention. Also, most preferred as pharmaceutically active ingredients are glipizide and diltiazem, verapamil, buspirone, tramadol and buproprion hydrochlorides.

Not to be bound by any theory, it is believed that the release of the pharmaceutically active ingredient within the present composition is provided due to the unique mixture of the rate controlling constituents and excipients in the selected ratios. When the composition is used as a matrix tablet, the solid nifedipine dissolves from the outer surface of the matrix tablet first. When this surface becomes exhausted of nifedipine, the underlying material begins to be depleted by dissolution and diffusion through the matrix to the external solution. During dissolution, some of the rate controlling constituents (the polymer blend) have a tendency towards swelling and thus act as a foci for cleavage or erosion of the matrix tablet. This leads to a cleavage of discrete amounts of nifedipine in combination with the rest of the excipients in the composition at the point of contact or interface between the rate controlling constituents and the other ingredients. In this manner, the interface between the region containing dissolved nifedipine and that containing dispersed nifedipine rescinds into the interior as a front. As the cleavage occurs, the nifedipine is readily absorbed. The release rate becomes smaller towards the end of dissolution due to a reduction in volume of the tablet.

When the composition is made and encased in coating material, the release of nifedipine is due to the encasement coat surrounding the homogeneous matrix tablet and the unique mixture of the rate controlling constituents and excipients in carefully selected ratios within the matrix tablet. Stepwise ionization of the surface groups of the encasement coat triggered by the pH of the surrounding media and the resulting gradual dissolution of the encasement coat over time exposes the matrix tablet to the fluids of the GI system. The solid nifedipine when in contact with the fluids of the GI system dissolves from the outer surface of the matrix tablet first. When this surface becomes exhausted of nifedipine, or other selected pharmaceutically active agent, the underlying material begins to be depleted by dissolution and diffusion through the matrix to the external solution.

The present composition provides controlled release of pharmaceutically active ingredient over an extended period of time (up to at least 20 hours) with minimal initial dumping effects, such that the active ingredient is still being released from the composition 20 hours later.

Furthermore, therapeutic agents may also be used in the composition of the present invention and are selected from the group consisting of anti-histamines, anti-depressants, anti-viral agents, anesthetics, antacids, anti-arthritics, antibiotics, anti-psychotics, anti-spasmodics, anxiolytic agents, appetite suppressants, cardiovascular agents, cough suppressants, emollients, gastro-intestinal agents, growth regulators, hypoglycemic agents, respiratory stimulants, vitamins, angiotensin converting enzyme inhibitors, anti-asthmatics, anti-cholesterolemics, anti-convulsants, anti-depressants, anti-diarrhea preparations, anti-infectives, anti-inflammatory agents, anti-nauseants, anti-stroke agents, anti-tumor drugs, anti-tussives, anti-uricemic drugs, amino-acid preparations, antiemetics, antiobesity drugs, antiparasitics, antipyretics, appetite stimulants, cerebral dilators, chelating agents, cholecystokinin antagonists, cognition activators, deodorants, dermatological agents, diabetes agents, diuretics, erythropoietic drugs, fertility agents, synthetic hormones, laxatives, mineral supplements, neuroleptics, neuromuscular agents, peripheral vasodilators, prostaglandins, vaginal preparations, vasoconstrictors and vertigo agents; acetaminophen, acetic acid, acetylsalicylic acid, buffered acetylsalicylic acid, albuterol, albuterol sulfate, ethanol isopropanol, allantoin, aloe, aluminum acetate, aluminum carbonate, aluminum chlorohydrate, aluminum hydroxide, alprozolam, amino acids, aminobenzoic acid amoxicillin, ampicillin, amsacrine, amsalog, anethole, aspartame, atenolol, bacitracin, balsam peru, beclomethasone dipropionate, benzocaine, benzoic acid, benzophenones, benzoylperoxide, biotin, bisacodyl, bornyl acetate, bromopheniramine maleate, buspirone, caffeine, calamine, calcium, calcium carbonate, calcium casinate, calcium hydroxide, camphor, captopril, cascara sagrada, castor oil, cefaclor, cefadroxil, cephalexin, cetylalcohol, cetylpyridinium chloride, chelated minerals, chloramphenicol, chlorcyclizine hydrochloride, chlorhexidine gluconate, chloroxylenol, chloropentostatin, chlorpheniramine maleate cholestyramine resin, choline bitartrate, cimetidine hydrochloride, cinnamedrine hydrochloride, citalopram, citric acid, cocoa butter, cod liver oil, codeine and codeine phosphate, clonidine, clonidine hydrochloride, clorfibrate, ciprofloxacin HCl, cyanocobalamin, cyclizine hydrochloride, danthron, dexbrompheniranime maleate, dextromethorphan hydrobromide, diazepam, dibucaine diclofenac sodium digoxin dimethicone, dioxybenzone, diphenhvdramine citrate, diphe ydrochloride, docusate calicum, docusate potassium, docusate sodium, doxycycline hyclate, doxylamine succinate, efaroxan, enalapril, enoxacin, erythromycin, estropipate, ethinyl estradiol ephedrine, epinephrine bitartrate, n, eucalyptol, ferrous fumarate, ferrous gluconate, ferrous sulfate, folic acid, fosphen3join, fluoxetine HCl, furosemide, gaba entan gentamicin, gemfibrozil, glipizide, glycerin, glyceryl stearate, izriseofulvin, guaifenesin, hexylresorcinol, hydrochlorothiaxide, hydrocodone bitartrate, hydrocortisone, hydrocortisone acetate, 8-hydroxyquinotine sulfate, ibuprofen, indomethacin, inositol, insulin, iodine, ipecac, iron, isoxicam, ketamine, koalin, lactic acid, lanolin, lecithin, lidocaine, lidocaine hydrochloride, lifinopril, liotrix, lovastatin, magnesium carbonate, magnesium salicylate, magnesium trisilocate, mefenamic acid, meclofenanic acid, meclofenamate sodium, medroxyprogesterone acetate, methenamine mandelate, menthol, meperidine hydrochloride, metaproterenol sulfate, methyl nicotinate, methyl salicylate, methylcellulose, methsuximide, metromidazole, metromidazole hydrochloride, metoprolol tartrate, miconazole nitrate, mineral oil, minoxidil, morphine, naproxen sodium, neomycin sulfate, niacin, niacinamide, nicotine, nicotinamide, nitroglycerin, nonoxynol-9, norethindone, norethindone acetate, nystatin, octoxynol, octyl dimethyl PABA, octyl methoxycinnamate, omega-3 polyunsaturated fatty acids, omeprazole, oxolinic acid, oxybenzone, oxtriphylline, para-aminobenzoic acid (PABA), padimate, paramethadione, pentastatin, peppermint oil, pentaerythriol tetranitrate, pentobarbital sodium, pheniramine maleate, phenobarbital, phenol, phenolphthalein, phenylephrine hydrochloride, phenylpropanolamine, phenylpropanolamine, hydrochloride, phenytoin, phenelzine, sulfate, pirmenol, piroxicam, polymycin B sulfate, potassium chloride, potassium nitrate, prazepam, procianamide hydrochloride, procaterol, propoxyphene, propoxyphene HCl, propoxyphene napsylate, pramiracitin, pramoxine, pramoxine hydrochloride, propronolol HCl, psedoephedrine hydrochloride, pseudoephedrine sulfate, pyridoxine, quinapril, quinidine gluconate, quinestrol ralitoline, ranitadine, resorcinol, riboflavin, salicylic acid, sesame oil, shark liver oil, simethicone, sodium bicarbonate, sodium citrate, sodium fluoride, sodium monofluorophosphate, sulfanethoxazole, sulfur, tacrine, tacrine HCl, theophylline, terfenidine, thioperidone, trimetrexate, triazolam, timolol maleate, tretinoin, tetracycline hydrochloride, tolmetin, tolnaftate, triclosan, triprolidine hydrochloride, undecylenic acid, vancomycin, vidaribine phosphate, vitamin A, vitamin B, vitamin C, vitamin D, vitamin E, vitamin K, witch hazel, xylometazoline hydrochloride, zinc, zinc sulfate, and zincundecylenate.

The compositions of the invention may be formulated in a tablet form or as a suppository. For both formulations, a coating composition can be optionally applied. Such a coating composition comprises anionic copolymers based on methacrylic acid and methyl methacrylate and are provided in an amount sufficient to obtain 0.5 to 15 mg per cm$^2$ on the tablet or suppository. This encasement coat, 0.5%–15% wt/wt, acts to minimize the initial burst effect seen in administered tableted compositions and also imparts gastrointestinal tract (GIT) "stealth" characteristics especially in the presence of food.

The present invention also provides a method for the manufacture of the novel controlled release pharmaceutical compositions in which the order and rate of drug release is dependant on the physicochemical properties and proportion of polymer blend and the wettability of the pharmaceutically active substance(s) such that sustained release effects are obtained therapeutically.

In a preferred embodiment, a two step granulation technique is used to prepare a desired controlled release device containing at least one selected active ingredient. The method comprises intragranulation by wet granulation and extragranulation by dry granulation. In the intragranulation process the pharmaceutically active substance is blended with about 5–25% hydroxypropyl methylcellulose (preferably METHOCEL® premium grade type K4M PREM), about 1–20% hydroxyethylcellulose (preferably NATROSOL® 250HHX), together with suitable pharmaceutical excipients such glidants e.g., silicone dioxide about (0.25–5%), surface active agents e.g., sodium lauryl sulfate about (0.5–15%), chanelling agents such as anhydrous lactose about (10–70%) and optionally a compression enhancer e.g., microcrystalline cellulose, AVICEL® 101 about (5–30%) until a homogeneous mixture is obtained. Blending can be done in a V-blender but preferably in a planetary or high shear mixer. The homogeneous blend is then granulated with isopropyl alcohol (99%) in a planetary or high shear mixer. It is preferred that the granulating solvent is a non aqueous solvent.

The wet granules are dried in a fluid bed or in tray dryers to a loss on drying of <3% and organic volatile impurities of isopropyl alcohol about <15000 ppm. The dry granules are milled to about <1500 microns using a cone mill. Thereafter the extragranular addition of 5–70% of ethylcellulose having 30–60% ethoxyl content and vicosity 60–100 cps (preferably ETHOCEL™ type N100) to the dry milled granules is undertaken in a V-blender until a homogeneous blend is obtained. To this blend may be added a glidant preferably talc and a lubricant preferably magnesium stearate. This final mixture is intimately blended and compressed into a matrix tablet using a rotary tablet press.

The matrix tablet can be used as is if no stealth characteristics are required. Under certain circumstances and for certain drugs, GIT stealth characteristics are desirable, e.g., in situations where dose dumping, burst or food effects are to be avoided. Stealth characteristics can be obtained by encasing the matrix tablet in a special coat composition consisting of anionic copolymer(s) based on methacrylic acid and methyl methacrylate. The preferred copolymers are the type A and/or Type B. This special composition may contain one or more of the following, plasticiser about (0–25%), pigment about (0–25%), glidant about (0–30%), lubricant about (0–30%). The values of dry polymer(s) encasing the matrix tablet in mg per cm² of surface area of tablet is about 0.5–15 mg per cm². This special stealth encasement may be applied using a fluid bed or a conventional coating pan. It is preferable to use a side vented perforated coating pan in order to obtain a more uniform and efficient encasement. The coating composition may be aqueous based, however, a solvent based composition is preferred.

EXAMPLES

The examples are described for the purposes of illustration and are not intended to limit the scope of the invention.

Methods of synthetic chemistry, and pharmacology referred to but not explicitly described in this disclosure and examples are reported in the scientific literature and are well known to those skilled in the art.

Example 1 - Glipizide ER 5 mg

| | % composition |
|---|---|
| Glipizide | 1.83 |
| Hydroxypropyl methylcellulose | 20 |
| Ethylcellulose | 16.17 |
| Hydroxyethylcellulose | 4 |
| Lactose | 30 |
| Microcrystalline cellulose | 23 |
| Silicone dioxide | 0.6 |
| Sodium Lauryl sulfate | 4 |
| Magnesium stearate | 0.4 |

Example 2 - Diltiazem hydrochloride ER 60 mg

| | % composition |
|---|---|
| Diltiazem hydrochloride | 58.82 |
| Hydroxypropyl methylcellulose | 5 |
| Ethylcellulose | 5 |
| Hydroxyethylcellulose | 15 |
| Lactose | 5 |
| Microcrystalline cellulose | 9.18 |
| Talc | 1 |
| Magnesium stearate | 1 |

Example 3 - Nifedipine ER 60 mg

| | % composition |
|---|---|
| Nifedipine | 20 |
| Hydroxypropyl methylcellulose | 20 |
| Ethylcellulose | 29 |
| Hydroxyethylcellulose | 3.8 |
| Lactose | 14 |
| Microcrystalline cellulose | 10 |
| Silicone dioxide | 1.2 |
| Na lauryl sulfate | 1 |
| Magnesium stearate | 1 |

Example 4 - Verapamil hydrochloride ER 60 mg

| | % composition |
|---|---|
| Verapamil HCl | 50 |
| Hydroxypropyl methylcellulose | 10 |
| Ethylcellulose | 5 |
| Hydroxyethylcellulose | 8 |
| Lactose | 16 |
| Microcrystalline cellulose | 10 |
| Magnesium stearate | 1 |

Example 5 - Diltiazem hydrochloride/Hydrochlorothiazide ER 60/12.5 mg

| | % composition |
|---|---|
| Diltiazem hydrochloride | 48 |
| Hydrochlorothiazide | 10 |
| Hydroxypropyl methylcellulose | 5.82 |
| Ethylcellulose | 5 |
| Hydroxyethylcellulose | 15 |

-continued

Example 5 - Diltiazem hydrochloride/Hydrochlorothiazide ER 60/12.5 mg

| | % composition |
|---|---|
| Lactose | 5 |
| Microcrystalline cellulose | 9.18 |
| Talc | 1 |
| Magnesium stearate | 1 |

Example 6 - Manufacturing method and composition of GIT "stealth" encasement

| | % composition |
|---|---|
| Methacrylic acid copolymer type A/B | 12 |
| PEG 600 | 2 |
| water | 5 |
| Talc | 8 |
| Titanium dioxide | 5 |
| Pigment | 8 |
| Ethanol | 60 |

Eudragit L/S was added to ethanol using a silverson high shear mixer (solution A). Secondly, PEG 600 was added to water using a propeller stirrer (solution B). Talc, pigment and titanium dioxide were added to ethanol (suspension C) using a propeller mixer. Solution B was added into suspension C and mixed vigorously. This mixture was then added to solution A under high shear mixing conditions to obtain the GIT "stealth" encasement.

Example 7 - Bupropion ER

| | % composition |
|---|---|
| Bupropion | 39 |
| Hydroxypropyl methylcellulose | 35 |
| Ethylcellulose | 5 |
| Hydroxyethylcellulose | 5 |
| Lactose | 10 |
| Microcrystalline cellulose | 5 |
| Silicone dioxide | 0.6 |
| Caprylocaproyl or oleoyl or linoleoyl macrogolglycerides | 5 |
| Magnesium stearate | 0.4 |

Example 8 - Buspirone hydrochloride ER 20 mg

| | % composition |
|---|---|
| Buspirone HCl | 5 |
| Hydroxypropyl methylcellulose | 35 |
| Ethylcellulose | 6 |
| Hydroxyethylcellulose | 15 |
| Lactose | 30 |
| Microcrystalline cellulose | 8 |
| Magnesium stearate | 1 |

Example 9 - Tramadol hydrochloride ER 200 mg

| | % composition |
|---|---|
| Tramadol hydrochloride | 37 |
| Hydroxypropyl methylcellulose | 33 |
| Ethylcellulose | 5 |
| Hydroxyethylcellulose | 5 |
| Lactose | 10 |
| Microcrystalline cellulose | 8 |
| Magnesium stearate | 1 |
| Talc | 1 |

Although preferred embodiments have been described herein in detail, it is understood by those skilled in the art that variations may be made thereto without departing from the scope of the invention or the spirit of the appended claims.

We claim:

1. A controlled release pharmaceutical composition comprising:
    (a) at least one pharmaceutically active substance having a water contact angle ($\theta$) such that cos $\theta$ is between +0.9848 and −0.9848;
    (b) a first intelligent polymer component comprising ethyl cellulose; and
    (c) a second intelligent polymer component having opposite wettability characteristics to said first intelligent polymer component, said second intelligent polymer component comprising a mixture of hydroxyethylcellulose and hydroxypropyl methyl cellulose, the first and second polymer components being present in a ratio in the range of about 1:100 to about 100:1 by weight,
    wherein said first and second polymer components are effective for providing controlled sustained release of said pharmaceutically active substance from said composition for up to at least 20 hours.

2. The composition of claim 1, wherein the first intelligent polymer component is more hydrophobic than the second intelligent polymer component.

3. The composition of claim 2, wherein the first intelligent polymer component is present in an amount not less than 5% by weight.

4. The composition of claim 1, further comprising at least one pharmaceutically acceptable excipient.

5. The composition of claim 4, wherein the excipient comprises 0.25% to 5% by weight of the composition.

6. The composition of claim 4, wherein the at least one excipient is silicon dioxide.

7. The composition of claim 1, wherein said composition further comprises 0.5% to 15% by weight of at least one surface active agent.

8. The composition of claim 7, wherein said surface active agent is sodium lauryl sulfate.

9. The composition of claim 1, wherein said composition further comprises 10% to 70% by weight channeling agents.

10. The composition of claim 9, wherein said channeling agent is anhydrous lactose.

11. The composition of claim 1, wherein said composition further comprises 5% to 30% compression enhancer.

12. The composition of claim 9, wherein said compression enhancer is microcrystalline cellulose.

13. A controlled release pharmaceutical composition comprising:

(a) from about 0.5% to about 70% by weight of a pharmaceutically active substance having a water contact angle (θ) such that cos θ is between +0.9848 and −0.9848;

(b) not less than about 5% by weight ethylcellulose;

(c) about 1:100 to 100:1 hydroxyethylcellulose and hydroxypropyl methyl cellulose by weight;

(d) about 0.25% to 5% excipients; and (e) about 0.5% to 15% surface active agents.

14. The composition of claim 13, wherein said composition additionally comprises about 10% to 70% channeling agents; and
about 5% to 30% compression enhancers.

15. The composition as claimed in claim 1, made in the form of a compressed tablet.

16. The tableted composition of claim 15, wherein said tableted composition has an anionic copolymer coating.

17. The tableted composition of claim 16, wherein said copolymer coating comprises methacrylic acid and methyl methacrylate, from about 0% to 25% plasticizer, from about 0% to 25% pigment, from about 0% to 30% glidant and from about 0% to 30% lubricant.

18. A controlled release composition, the composition comprising a therapeutically effective amount of a pharmaceutically active ingredient having a water contact angle (θ) such that cos θ is between +0.9848 and −0.9848; two groups of intelligent polymers having opposing wettability characteristics, one group demonstrating a stronger tendency towards hydrophobicity and present in an amount not less than 5% wt/wt and the other group having a stronger tendency towards hydrophilicity and present in the ratio of about 1:100 and 100:1, the polymers being ethylcellulose (EC) as a more strongly hydrophobic and hydroxyethylcellulose (HEC) and hydroxypropyl methylcellulose (HPMC) as more strongly hydrophilic, about 0.25% to 5% silicon dioxide; and about 0.5% to 15% sodium lauryl sulfate.

19. The composition of claim 18, wherein said composition additionally comprises about 10% to 70% anhydrous lactose and about 5% to 30% microcrystalline cellulose.

20. The composition of claim 17, wherein said composition is provided as a tablet and has a coating composition comprising anionic copolymers sufficient to obtain about 0.5 to 15 mg per cm² of tablet.

21. The composition of claim 20, wherein said coating composition additionally comprises from about 0 to 25% plasticizer, about 0 to 25% pigment, about 0 to 30% glidant and about 0 to 30% lubricant.

22. A process for the manufacture of a sustained release composition of pharmaceutically active substance, said process comprising:

(a) admixing a pharmaceutically active substance having a water contact angle (θ) such that cos θ is between +0.9848 and −0.9848;

(b) blending the pharmaceutically active ingredient with about 5 to 25% hydroxypropyl methylcellulose, about 1 to 25% hydroxyethylcellulose, about 0.25% to 5% suitable pharmaceutical excipients, about 0.5% to 15% suitable surface active agents, and about 10% to 70% chanelling agents in a high shear mixer until a homogeneous mixture is obtained;

(c) granulating the homogeneous blend with isopropyl alcohol (99%) in a planetary or high shear mixer;

(d) drying the wet granules to a loss on drying of about <3% and organic volatile impurities of isopropyl alcohol about <15000 ppm;

(e) milling the dry granules to about <1500 microns;

(f) adding and blending about 5% to 70% of ethylcellulose having 30–60% ethoxyl content and a vicosity of 60–100 cps to the dry milled granules until a homogeneous blend is obtained;

(g) adding and intimately mixing a lubricant, and optionally a glidant and optionally a compression enhancer;

(h) compressing the lubricated granules into tablets having a hardness of 5–30 Strong Cobb units and a moisture content of about <5% with a rotary tablet press; and (i) optionally encasing the matrix tablet in a GIT "stealth" encasement or a pharmaceutically acceptable film coat.

23. The process according to claim 22, wherein said "stealth" encasement comprises anionic copolymer(s) of methacrylic acid and methyl methacrylate and one or more of the following, plasticiser (about 0–25%), titanium dioxide (about 0–25%), pigment (about 0–25%), glidant (about 0–30%), and lubricant (about 0–30%).

24. The composition of claim 1, encased in a "stealth" encasement formed by a process comprising preparing a first solution of methacrylic acid copolymer type A and/or type B in ethanol, preparing a second solution of PEG 600 in water, adding talc, pigment and titanium dioxide to the first solution and then incorporating the second solution and mixing vigorously under high shear mixing conditions.

25. The composition of claim 1, wherein said pharmaceutically active substance is nifedipine having a specific surface area of <0.5 m²/gram or >6 m²/gram.

26. The composition of claim 1, wherein the composition is provided as a tablet which demonstrates the following cumulative percent release dissolution criteria using a pH gradient method of dissolution; 0–40% released in 1 hour in dissolution media of pH 1.50, 0–50% released in 2 hours in dissolution media of pH 4.5, 5–70% released in 2 hours in dissolution media of pH 6.5, 20–100% released in 15 hours in dissolution media of pH 7.5.

27. The composition of claim 1, wherein the pharmaceutically active substance is selected from the group consisting of nifedipine, glipizide, diltiazem hydrochloride, bupropion, buspirone hydrochloride, tramadol hydrochloride and verapamil HCl.

28. The composition of claim 1, wherein the pharmaceutically active substance is selected from the group consisting of nicardipine, felodipine, captopril, naproxen, diclofenac, terfenadine, pentoxifylline, fenofibrate, glipizide, buspirone, cisapride, verapamil, diltiazem, aciclovir, zidovudine, pilocarpine, moclobemide, lamotrigine, risperidon, clonazepam, nefazodone, lovastatin, simvastatin, pravachol, ketorolac, hydromorphone, morphine, ticlopidine, seligiline, venlafaxine, alprazolam, carbamazepine, divalproex and phenytoin.

29. A controlled release pharmaceutical composition comprising:

(a) at least one pharmaceutically active substance having a water contact angle (θ) such that cos θ is between +0.9848 and −0.9848;

(b) a first intelligent polymer component comprising ethylcellulose; and (c) a second intelligent polymer component having opposite wettability characteristics to said first intelligent polymer component, said second intelligent polymer component comprising a mixture of hydroxyethylcellulose and hydroxypropyl methyl cellulose, the first and second polymer components being present in a ratio in the range of about 1:100 to about 100:1 by weight;

wherein said first and second polymer components are effective for providing controlled sustained release of said pharmaceutically active substance from said composition for up to at least 20 hours; and wherein components (a), (b) and (c) are formulated as a homogeneous matrix and said composition has a moisture content of less than 3%.

30. The composition of claim 1, wherein the first and second polymer components are effective for providing controlled sustained release of such pharmaceutically active substance from said composition for at least 15 hours.

31. The composition of claim 29, wherein the first and second polymer components are effective for providing controlled sustained release of such pharmaceutically active substance from said composition for at least 15 hours.

32. A controlled release pharmaceutical composition comprising:

(a) at least one pharmaceutically active substance having a water contact angle ($\theta$) such that cos $\theta$ is between +0.9848 and −0.9848;

(b) a first intelligent polymer component comprising ethylcellulose; and (c) a second intelligent polymer component having opposite wettability characteristics to said first intelligent polymer component, said second intelligent polymer component comprising a mixture of hydroxyethylcellulose and hydroxypropyl methyl cellulose, the first and second polymer components being present in a ratio in the range of about 1:100 to about 100:1 by weight, wherein said first and second polymer components are effective for providing controlled sustained release of said pharmaceutically active substance from said composition.

33. A controlled release pharmaceutical composition comprising:

(a) at least one pharmaceutically active substance having a water contact angle ($\theta$) such that cos $\theta$ is between +0.9848 and −0.9848;

(b) a first intelligent polymer component comprising ethylcellulose;

(c) a second intelligent polymer component having opposite wettability characteristics to said first intelligent polymer component, said second intelligent polymer component comprising a mixture of hydroxyethylcellulose and hydroxypropyl methyl cellulose, the first and second polymer components being present in a ratio in the range of about 1:100 to about 100:1 by weight;

wherein said first and second polymer components are effective for providing controlled sustained release of said pharmaceutically active substance from said composition; and wherein components (a), (b) and (c) are formulated as a homogeneous matrix and said composition has a moisture content of less than 3%.

34. The process according to claim 22, wherein the lubricant comprises magnesium stearate, and/or wherein the glidant comprises talc.

* * * * *